US006805683B1

United States Patent
Johansson

(12) United States Patent
(10) Patent No.: US 6,805,683 B1
(45) Date of Patent: Oct. 19, 2004

(54) MICRODIALYSIS PROBE

(75) Inventor: Roger Johansson, Knivsta (SE)

(73) Assignee: CMA/Microdialysis AB, Solna (SE)

( * ) Notice: Subject to any disclaimer, the term of this patent is extended or adjusted under 35 U.S.C. 154(b) by 341 days.

(21) Appl. No.: 10/030,922

(22) PCT Filed: Jul. 14, 2000

(86) PCT No.: PCT/SE00/01496

§ 371 (c)(1),
(2), (4) Date: May 10, 2002

(87) PCT Pub. No.: WO01/03763

PCT Pub. Date: Jan. 18, 2001

(30) Foreign Application Priority Data

Jul. 14, 1999 (SE) .............................. 9902694

(51) Int. Cl.[7] .......................................... A61M 37/00
(52) U.S. Cl. ................... 604/6.16; 604/4.01; 604/529; 604/27; 210/645; 210/650
(58) Field of Search ..................... 604/4.01, 5.01–5.04, 604/6.09, 6.16, 19, 27, 28–29, 39, 43, 500, 506–508, 264, 268, 523, 529, 532–35; 210/645–647, 650–652, 348, 321.6, 321.61, 321.72, 321.87–321.89; 128/898

(56) References Cited

U.S. PATENT DOCUMENTS

| 5,106,365 A | * | 4/1992 | Hernandez .................... 604/27 |
| 5,191,900 A | * | 3/1993 | Mishra ........................ 600/585 |
| 5,607,390 A | * | 3/1997 | Patsalos et al. ............... 604/29 |
| 6,030,358 A | * | 2/2000 | Odland ........................ 604/27 |
| 6,478,767 B1 | * | 11/2002 | O'Connell .................... 604/27 |

FOREIGN PATENT DOCUMENTS

| EP | 0 702 976 A1 | 3/1996 |
| EP | 0 807 444 A2 | 11/1997 |
| WO | WO 95/20983 | 8/1995 |

* cited by examiner

Primary Examiner—Patricia Bianco
(74) Attorney, Agent, or Firm—Young & Thompson

(57) ABSTRACT

A microdialysis probe includes a dialysis membrane located and supported between a closed distal end of the probe and a proximal end of the same, which membrane essentially-surrounding a space for passage of perfusion liquid. The probe has an inlet and outlet for perfusion liquid. The probe exhibits a deformable mesh sleeve adapted to enclose and protect at least the dialysis membrane, the proximal end of the deformable being fastened to the probe between the proximal end of the probe and the dialysis membrane.

9 Claims, 4 Drawing Sheets

MICRODIALYSIS PROBE

FIELD OF THE INVENTION

The invention relates to a microdialysis probe. Dialysis probes of this kind are described in SE-C-434 214, U.S. Pat. No. 5,735,832 and U.S. Pat. No. 5,741,284.

The meaning of specific wordings in this text should be interpreted as follows: The word probe should be interpreted also as catheter. The inlet and outlet of the probe as described may in case of a reversed flow be used as outlet and inlet, respectively.

Perfusion liquid is the liquid used in the microdialysis, which is allowed to enter the probe and there take up substances from the surrounding tissue through a membrane. The perfusion liquid becomes the dialysate after the dialysis. Deformable mesh is to be interpreted as further described in the application below.

BACKGROUND OF THE INVENTION

Microdialysis is a method of examination in which a probe is inserted into tissue in vivo, such that one side of a semi-permeable membrane is in contact with tissue and extra cellular liquid and the other side is flushed or rinsed with a dialysis liquid (perfusate) which takes-up substances from the extra cellular liquid through the membrane. These substances can then be analyzed in the dialysate on or after exiting the probe.

Microdialysis probes are by nature fragile, which requires great care in inserting and withdrawing the probe from the tissue in which it is used. At least part of the probe needs to have a surface consisting of a thin permeable membrane, which may be broken particularly when removing the probe. For insertion of the probe there exists insertion means such as an external tube or the like that may be used to protect the probe during insertion. The insertion means, if such means are used, are removed before the actual use of the probe if such are used.

However, when inserted into tissue of a living person, the probe must be able to retain its shape despite the stresses and strains to be expected when/if the person moves (even if the person is quite still there may still be movements in e.g. a muscle) and at withdrawal of the probe.

The use of microdialysis becoming more frequent and common raises other problems such as monitoring and control of the probe during insertion and use. It is a fact that microdialysis provides a unique possibility to examine the equilibrias of substances and/or the amounts present or missing of substances or to monitor specific changes in the status of substances connected with e.g. the use of medicaments, in surgery etc.

The monitoring and control of the probe position during insertion/withdrawal and use has been an obstacle in so far that the smallness and the material of the probe does not make possible the use of common methods for detecting the probe once the insertion has been started. This becomes more problematic the deeper into the tissue the microdialysis is to take place.

SUMMARY OF THE INVENTION

It is thus an object of the invention to provide a microdialysis probe, which is suitable for the general use in living tissue when taking samples for e.g. diagnostic purposes. In particular the object is an improved probe, which may withstand forces acting on the probe during use and withdrawal of the same.

A further object is to give good access to the membrane for the intracellular liquid and still be able to protect the membrane and to be able to retract the probe in full.

A further object of the invention is to provide a microdialysis probe, the location of which may be monitored and controlled using means such as X-rays or the like during insertion/withdrawal or during dialysis in order to facilitate the placement of the probe at a predetermined location and to control the location of the probe.

In accordance with the invention, these and other objects evident from the description of the invention are accomplished in a microdialysis probe in that a deformable mesh sleeve is adapted to enclose and protect at least said dialysis membrane, the proximal end of said deformable sleeve fastened to the probe between the proximal end of the probe and the dialysis membrane, and in that said deformable mesh sleeve when subjected to a pulling action in the longitudinal direction of the sleeve is deformed such that the diameter of said sleeve decreases.

The wording enclose should be understood such that the mesh sleeve always is secured to the proximal part of the probe but the other end of the sleeve may be either open-ended or closed or attached to the distal part of the probe as such.

BRIEF DESCRIPTION OF THE DRAWINGS

The invention will now be described by way of example and with reference to the accompanying drawings in which.

a. probe exhibiting a first embodiment of the mesh sleeve according to the invention.

b. probe exhibiting a mesh sleeve also according to the first embodiment.

c. probe exhibiting a second embodiment of the mesh sleeve according to the invention.

d. probe exhibiting a second embodiment of the mesh sleeve according to the invention.

FIG. 2 shows an example of the mesh-type preferably used according to the invention.

FIGS. 3 a–b illustrates the changes in the deformable mesh sleeve dimensions a) unaffected.

b) affected.

Figure 4:
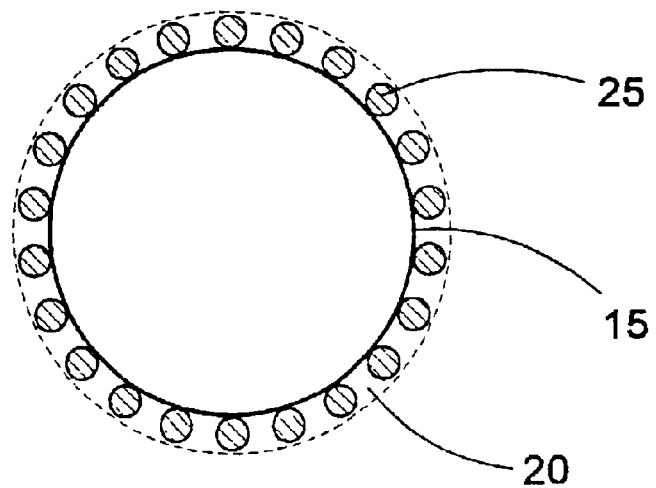

FIG. 4 shows a cross section of a probe according to the invention.

DETAILED DESCRIPTION OF PREFERRED FORMS OF THE INVENTION

Throughout FIGS. 1a–1d like details are designated with corresponding numerals.

Figure 1A:
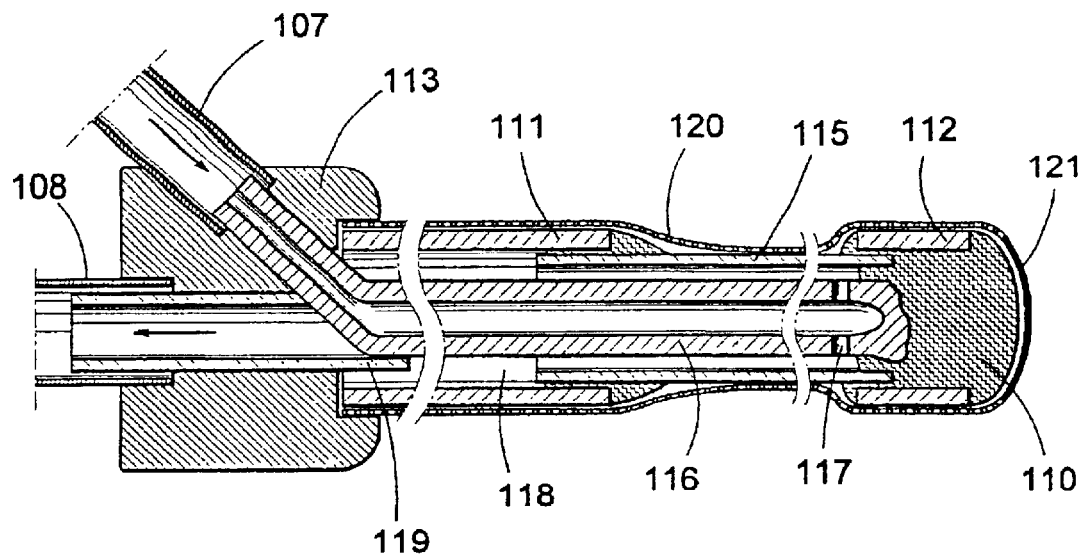
FIGS. 1 a–d shows four examples of a microdialysis probe in section exhibiting the mesh sleeve according to the invention.

A first embodiment of the microdialysis probe according to the invention is shown in FIG. 1a. The probe exhibits a distal end piece 110 and a distal tubular fitting 112. The distal tubular fitting 112 in combination with the end piece 110 comprises the foremost tip of the probe. A proximal tubular fitting 111 and a proximal end piece 113 comprises the other end of the probe as such. The proximal tubular fitting 111 is permanently fastened to a proximal end piece 113. A membrane 115 is fastened to the distal tubular fitting 112, the membrane 115 having a smaller diameter than the fitting. The membrane is preferably tubular. The fitting itself being closed at the most distal end thereof e.g. by using glue or the like, forming the distal end 110. The other end of the membrane 115 is fastened to the proximal tubular fitting 111. It should be understood that the above describes an exemplary embodiment of the distal end of the probe itself and the constructive details thereof may vary within the scope of the claims or be independent of the constructive details of the distal end of the probe depending on different embodiments of the invention.

In the end proximal piece 113 two tubes 107 and 108 constituting the inlet to the probe and the outlet from the probe are connected to the probe, such as to let the perfusion liquid pass through the same. Note above the possibility of reversed flow.

To give a proper understanding of the invention, exemplary dimensions are given here. The length of the probe may be e.g. 5 cm from the most distal end of the same to the proximal part of the proximal tubular fitting 111. The length of the tubular fitting may be approximately 2 cm, thus the length of the membrane may be approximately 3 cm. The diameter of the proximal tubular fitting may be approximately 1 mm and the outer diameter of the membrane may be approximately 0.6 mm.

These dimensions imply that the parts of the probe especially the membrane is very thin. The membrane is e.g. made from polyamide and the tensile strength of the same is hard to measure properly in that it is easily ruptured. Such membranes are i.a. manufactured by Gambro AB, Sweden.

Within the membrane 115, which is in the form of a tube made from semi-permeable material, first tube 116 extends essentially from the proximal end of the probe to the distal end. The first tube 116 has a closed distal end and has at least one aperture 117 at or near the distal end. The aperture 117 constitutes a passage for the perfusion liquid entering the space 118 defined by the first tube 116 and the dialysis membrane 115 in combination with the proximal tubular fitting 111 and the distal tubular fitting 112. For the withdrawal of the perfusion liquid a second tube 119 extends from the proximal end of the probe and opens up into the same space 118 somewhere near to the to the proximal end of the probe thereby forming an exit for the perfusion liquid. The perfusion liquid has now become a dialysate having acquired substances exchanged over the semi-permeable membrane. The distal end piece 110 of the probe may e.g. be fastened in a permanent way to the distal end of the first tube 116.

According to the invention a protective definable mesh sleeve 120 surrounds said dialysis membrane 115, said protective sleeve adapted to enclose said dialysis membrane 115. The most distal end 121 of the sleeve 120 has been closed so as to form a sack-like container into which the probe is inserted and secured at the proximal end thereof. The distal end of the sleeve is secured between the proximal tubular fitting 111 and the end proximal piece 113.

In this manner the sleeve can be safely retracted in the same operation as the retraction of the probe and the sleeve will be the safeguard that all of the probe will be reclaimed upon retraction.

Figure 1B:
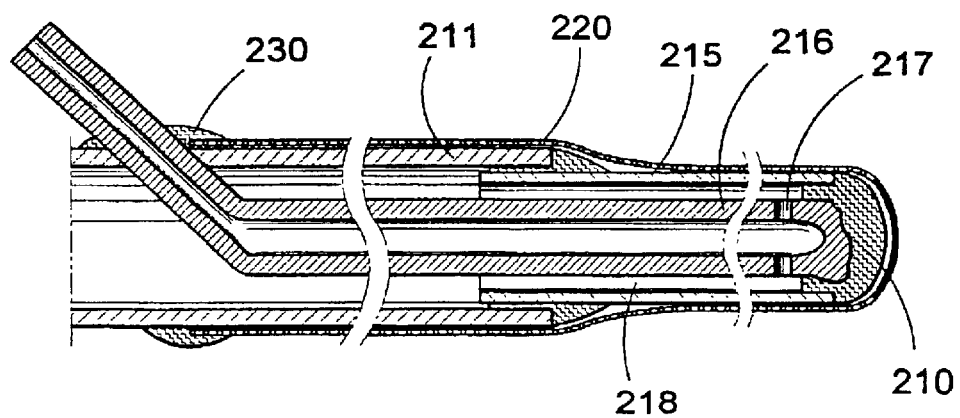

In FIG. 1b a second embodiment of the probe having a different construction and depending thereon another construction of the sleeve is shown. The probe exhibits a distal end piece 210. The end piece 210 comprises the foremost tip of the probe. A proximal tube 211 comprises the other end of the probe as such. The most proximal part of the probe is not shown in the drawing.

A tube-like membrane 215 is fastened to the distal end piece 210. The membrane 215 itself being closed at the most distal end thereof e.g. by using glue or the like, forming the distal end 210. The other end of the membrane 115 is fastened to the proximal tube 211.

Within the membrane 215, which is in the form of a tube made from semi-permeable material, a first tube 216 extends essentially from the proximal end of the probe to the distal end. The first tube 216 has a closed distal end and has at least one aperture 217 at or near the distal end. The aperture 217 constitutes a passage for the perfusion liquid entering the space 218 defined by the first tube 216 and the dialysis membrane 215. For the withdrawal of the perfusion liquid a second tube (not shown) extends from the proximal end of the probe and opens up into the same space 118 somewhere near to the to the proximal end of the probe thereby forming an exit for the perfusion liquid. The proximal tube 211 itself may constitute the exit part from the probe. The perfusion liquid enters the probe through the first tube 216, which is shown to enter the second tube through the wall of the same. The distal end piece 210 of the probe may e.g. be fastened in a permanent way to the distal end of the first tube 216.

The protective deformable mesh sleeve 220 surrounds said dialysis membrane 215, said protective sleeve adapted to enclose said dialysis membrane 215. The most distal end 221 of the sleeve 220 has been closed so as to form a sack-like container into which the probe is inserted and is secured at the proximal end thereof. The open end of the sack-like sleeve-container 220 has been fastened to the outside of the tubular fitting 211 by glue or the like 230. The fastening of the sleeve 220 to the tubular fitting 211 is preferably done in the vicinity of the through-hole for the first tube 216 such as to be able to perform the fastening and the sealing of the edges of the through-hole against the first tube 216 in one operation.

Figure 1C:
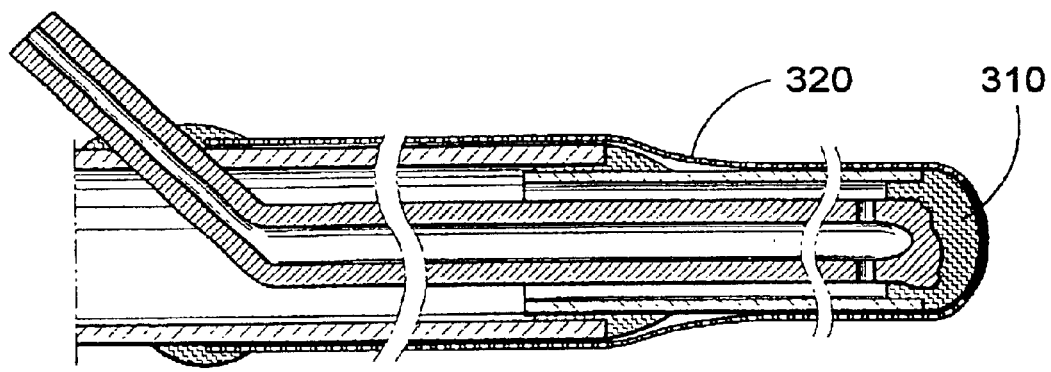

In FIG. 1c the same type of probe is used as in FIG. 1b. The embodiment shown differs from the one in FIG. 1b in that the deformable mesh sleeve 320 is fastened to the distal end piece 310 by glue or by fusing the material of the end piece 310, the membrane 315, the most distal part of the deformable mesh sleeve 320 in one or more steps, thereby forming the most distal part of the probe as one unit.

Figure 1D:
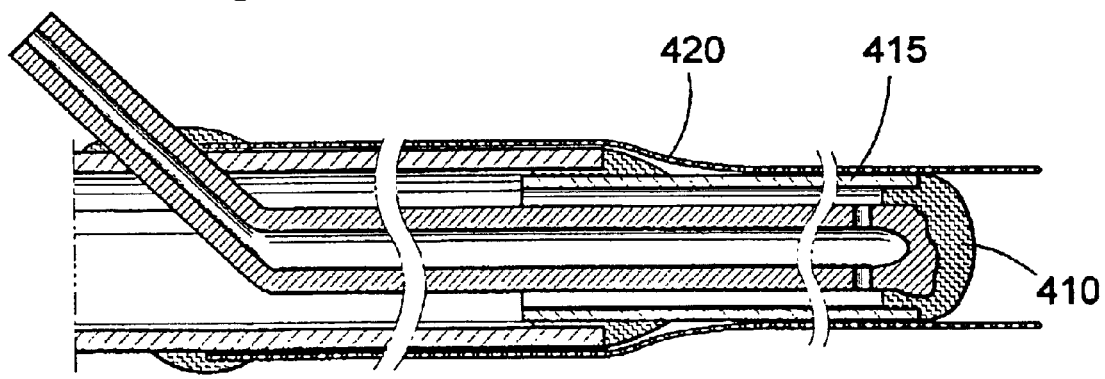

In FIG. 1d a further embodiment of the invention is shown. The probe shown is essentially identical to the one in FIGS. 1b and 1c. The difference between the embodiments is that the distal end of the deformable mesh sleeve 420 is not closed at all but leaves the end piece 410 free from connection with the sleeve 420. This embodiment still works in the same manner as the preceding embodiments in that when the probe is retracted the sleeve will be held back by the tissue and thus will show a decreasing diameter, thus ensuring that all of the probe will be retractable.

The insertion of this last embodiment in a muscle or the like is preferably performed using an instrument adapted to assist in the insertion and thereafter be removed. Such device per se are known within the art and are not the subject of this invention.

The protective deformable mesh sleeve used according to the invention may be formed from an elastic mesh of the type were the threads of the mesh in an unaffected state meet each other under predetermined angel forming diamond like openings in the mesh. When exerting force essentially the general direction of the sleeve the mesh in an effected state may be pulled out such as to decrease the acute angle and to shorten the mesh in the direction perpendicular to the thrust line i.e. to decrease the diameter of the sleeve will serve to brace the probe, i.e. especially the membrane part of the same and to hinder the probe from breaking. Any arrangement of threads which will perform as described above are suitable for use according to this invention. The mesh could thus be also a woven fabric which exhibits approximately the same characteristics as to deforming.

The shortening of the mesh in the direction perpendicular to the first line is the reason explaining that the embodiment in FIG. 1d will function even though that the distal end of the sleeve is open. When retracting the probe having the deformable sleeve, the diameter of the sleeve will decrease, thus holding the probe together and hindering the probe from breaking.

Figure 2A:
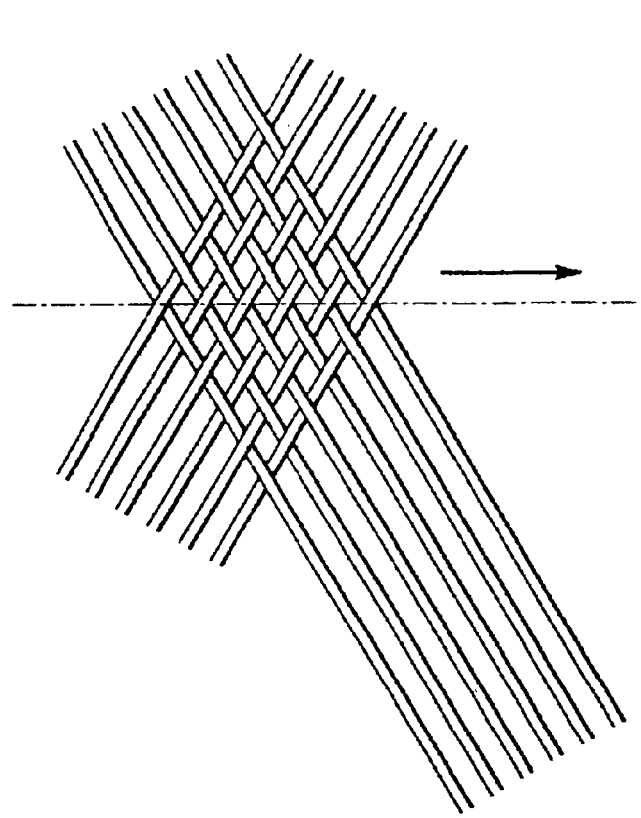
Figure 2B:
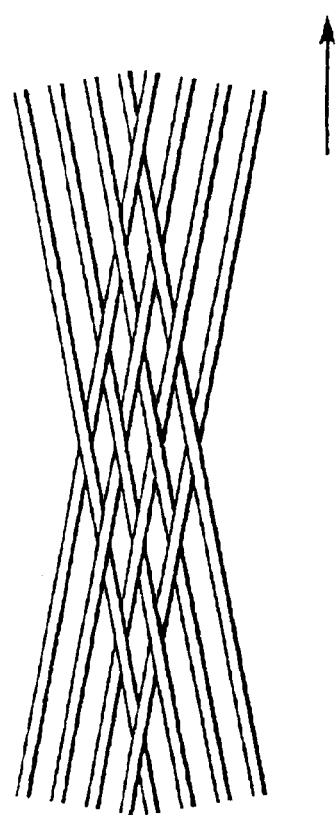

Examples of the mesh in the protective sleeve is shown in FIGS. 2a–b, where in FIG. 2a is shown a braided mesh, which may be expanded in one of two perpendicular directions, using tensile forces. Such a material formed as a sleeve or a tube and having a predetermined circumference in a non-stretched stated, will upon pulling forces applied in the longitudinal direction of the tube become stretched and the circumference will contract.

A probe according to the invention thus will be held together as one unit under all circumstances.

Figure 3A:
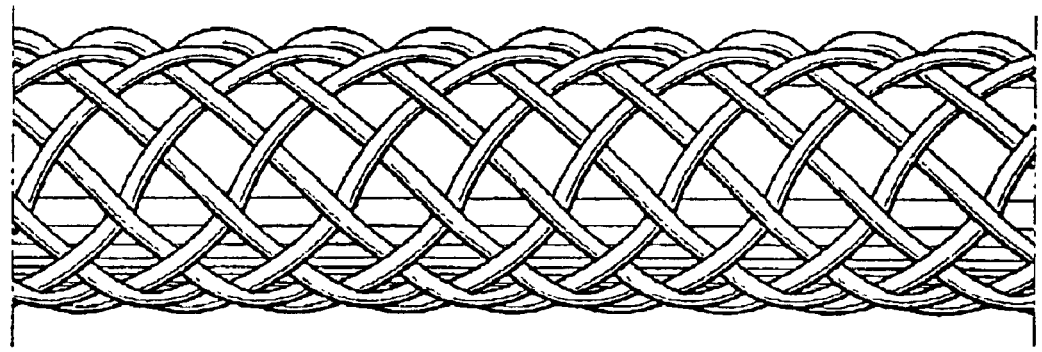
Figure 3B:
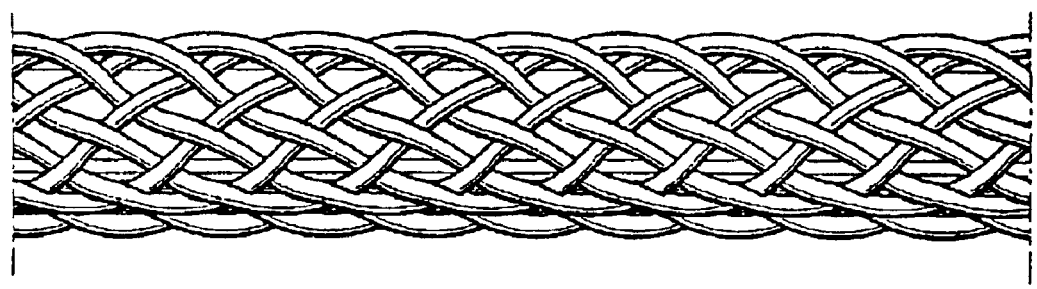

In FIG. 3 the changes in the deformable mesh sleeve dimensions as unaffected and affected is shown. The dimensional changes of the sleeve as "unaffected" in FIG. 3a may be compared with the affected stated shown in FIG. 3b where the sleeve has been subjected to a stretching movement and thus has enclosed the probe more tightly than in FIG. 3a.

It should, however, be noted that the state of the deformable sleeve shown in FIG. 3a may e.g. still be in an affected state in the sense that the sleeve in order to fit over the probe has to a certain degree been stretched in the circumferential direction. I.e. the sleeve may, before fitting the same over the probe, have exhibited a smaller circumference than the probe.

The mesh sleeve protects the probe when used in a muscle or in any other living tissue. When used for the purpose of e.g. continued monitoring the probe according to the invention is used in living tissue, which means that forces will be exerted on the probe by the surrounding tissue during the microdialysis. In a few cases this may cause harm to the membrane such as to give fissure or the like in the membrane. The important aspect is to be able to remove the entire probe in one operation, the fissured probe held together by the protective sleeve. A good measure of the improvement gained by the probe according to the invention is, that the mesh sleeve shows a tensile strength of approximately 10–20 N, as compared with the membrane itself, the strength of which is discussed above as being very small.

A cross section of a probe according to the invention in the area of the membrane is shown in FIG. 4. In the figure the first and the second rubes are not shown, but only the surrounding membrane 15 and the mesh threads 25 making up the deformable mesh sleeve 20 are shown. As can be seen in the figure the mesh sleeve 20 leaves access to the membrane 15 from the tissue side of the same. In-between the filaments making up the material in the sleeve there is enough space for the membrane to make good contact with the extra-cellular liquid. This vouches for a good contact and a good recovery resulting from the microdialysis.

In the probe according to the invention a further improvement is achieved by introducing into the mesh a predetermined amount of e.g. metal-ions or metal such that the probe will be opaque to X-rays. The metal would preferably have to be introduced in the material making up the probe and be dispersed therein in elemental form i.e. as metal or as a part of one of the compounds from which the mesh is manufactured.

In further embodiment the metal may be dispersed in at least one of the threads making up the material. There is also the possibility of substitution of one or more of the plastic material thread by a metallic thread. The invention has been described under reference to embodiments of the same. The scope of the invention however is described by the appended claims.

What is claimed is:

1. A microdialysis probe, comprising a dialysis membrane (115,215,315,415) located and supported between a closed distal end of the probe and a proximal end of the same, said membrane (115,215,315,415) essentially surrounding a space (118,218,318,418) for passage of perfusion liquid; said probe having input and output means (107,108;207,208;307,308;407,408) for perfusion liquid; characterized by a deformable mesh sleeve (120,220,320,420) adapted to enclose and protect at least said dialysis membrane (115,215,315,415) a proximal end of said deformable sleeve fastened to the probe between the proximal end of the probe and the dialysis membrane (115,215,315,415).

2. Microdialysis probe according to claim 1, characterized in that said deformable mesh sleeve (120,220,320,420) being X-ray opaque through the addition of substances to the material forming the deformable mesh sleeve (120,220,320,420) giving the material such characteristics.

3. Microdialysis probe according to claim 2, characterized in that said substance is a metal dispersed in the material forming the deformable mesh sleeve (120,220,320,420).

4. Microdialysis probe according to claim 2, characterized in that said substance is a metal-ion comprised in one of or in the compound of the material forming the deformable mesh sleeve (120,220,320,420).

5. Microdialysis probe according to claim 1, characterized in that said deformable mesh sleeve (120,220) has a closed distal end (120,221) surrounding the distal end (110,210) of the probe.

6. Microdialysis probe according to claim 1, characterized in that said deformable mesh sleeve (320) has a closed distal end unitary with the distal end (310) of the probe.

7. Microdialysis probe according to claim 1, characterized in that said deformable mesh sleeve (420) has an open distal end.

8. Microdialysis probe according to claim 1, characterized in that said deformable mesh sleeve when subjected to a pulling action in the longitudinal direction of the sleeve (120,220,320,420) is deformed such that the diameter of said sleeve decreases.

9. Microdialysis probe according to claim 1, characterized said deformable mesh sleeve (120,220,320,420) being X-ray opaque through the substitution of or inclusion of x-ray opaque filaments in the material making up the mesh material.

* * * * *